(12) United States Patent
Cettina et al.

(10) Patent No.: US 11,202,722 B2
(45) Date of Patent: *Dec. 21, 2021

(54) EXTENSIBLE DRESSINGS

(71) Applicant: Johnson & Johnson Consumer Inc., Skillman, NJ (US)

(72) Inventors: Melinda Cettina, Robbinsville, NJ (US); Paulo Oriani, Sao Paulo (BR); Fabio Eduardo F. Rangel, Sao Paulo (BR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 300 days.

This patent is subject to a terminal disclaimer.

(21) Appl. No.: 16/129,716

(22) Filed: Sep. 12, 2018

(65) Prior Publication Data

US 2019/0099297 A1  Apr. 4, 2019

Related U.S. Application Data

(60) Provisional application No. 62/576,210, filed on Oct. 24, 2017, provisional application No. 62/565,604, filed on Sep. 29, 2017.

(51) Int. Cl.
*A61F 13/02* (2006.01)
*A61F 13/511* (2006.01)
(Continued)

(52) U.S. Cl.
CPC ........ *A61F 13/0206* (2013.01); *A61F 13/022* (2013.01); *A61F 13/0226* (2013.01);
(Continued)

(58) Field of Classification Search
CPC ............... A61F 13/0206; A61F 13/022; A61F 13/0226; A61F 13/0243; A61F 13/0246; A61F 13/0259; A61F 13/51121; A61F 13/5116; A61F 2013/00089; A61F 2013/5113; A61F 2013/51139; A61F 2013/51147; A61F 2013/51143; A61F 2013/51178; A61F 2013/0077; A61F 2013/00774; A61F 13/00029;
(Continued)

(56) References Cited

U.S. PATENT DOCUMENTS 2,811,154 A   10/1957  Scholl
RE24,906 E   12/1960  Ulrich
(Continued)

FOREIGN PATENT DOCUMENTS

EP   617938 A    10/1994
EP   0676183 A1  10/1995
(Continued)

OTHER PUBLICATIONS

Partial European Search Report; Appln. No. 18197737.2-1102; dated Feb. 28, 2019.
(Continued)

*Primary Examiner* — Camtu T Nguyen

(57) ABSTRACT

The present invention relates to dressings such as bandages improved extensibility. The present invention further relates to dressings comprising an absorbent body and backing layer having improved extensibility.

14 Claims, 10 Drawing Sheets

(51) Int. Cl.
*A61F 13/00* (2006.01)
*D04H 1/728* (2012.01)

(52) U.S. Cl.
CPC ...... *A61F 13/0243* (2013.01); *A61F 13/0246* (2013.01); *A61F 13/0259* (2013.01); *A61F 13/5116* (2013.01); *A61F 13/51121* (2013.01); *A61F 2013/00089* (2013.01); *A61F 2013/5113* (2013.01); *A61F 2013/51139* (2013.01); *A61F 2013/51143* (2013.01); *A61F 2013/51147* (2013.01); *A61F 2013/51178* (2013.01); *D04H 1/728* (2013.01)

(58) Field of Classification Search
CPC .............. A61F 13/00038; D04H 1/728; B32B 37/1284; B32B 37/1292
See application file for complete search history.

(56) References Cited

U.S. PATENT DOCUMENTS

| | | | |
|---|---|---|---|
| 3,389,827 A | 6/1968 | Abere et al. | |
| 3,888,247 A | 6/1975 | Stenvall | |
| 4,112,213 A | 9/1978 | Waldman | |
| 4,310,509 A | 1/1982 | Berglund et al. | |
| 4,323,557 A | 4/1982 | Rosso et al. | |
| 4,472,480 A | 9/1984 | Olson | |
| 4,538,603 A | 9/1985 | Pawelchak et al. | |
| 4,561,435 A | 12/1985 | McKnight et al. | |
| 4,655,768 A | 4/1987 | Marecki et al. | |
| 4,737,410 A | 4/1988 | Kantner | |
| 6,264,976 B1 | 7/2001 | Heinecke | |
| 6,838,589 B2 | 1/2005 | Liedtke et al. | |
| 6,927,315 B1 | 8/2005 | Heinecke et al. | |
| 7,030,288 B2 | 4/2006 | Liedtke et al. | |
| 7,612,248 B2 | 11/2009 | Burton et al. | |
| 9,445,951 B2 | 9/2016 | Moberg-Alehammar et al. | |
| 10,016,310 B2 | 7/2018 | Caneppele et al. | |
| 10,034,799 B2 | 7/2018 | Caneppele et al. | |
| 2002/0019372 A1* | 2/2002 | Schnellmann | A61K 31/665 514/99 |
| 2002/0077578 A1 | 6/2002 | Bonutti | |
| 2003/0093024 A1 | 5/2003 | Falleiros et al. | |
| 2004/0241215 A1 | 12/2004 | Lipman | |
| 2006/0004335 A1 | 1/2006 | Wang et al. | |
| 2006/0173087 A1* | 8/2006 | Hyde | A61L 15/60 521/82 |
| 2008/0171958 A1* | 7/2008 | Gundersen | A61F 13/022 602/56 |
| 2009/0216168 A1 | 8/2009 | Eckstien | |
| 2010/0204667 A1 | 8/2010 | Chakravarthy | |
| 2011/0054429 A1 | 3/2011 | Lademann et al. | |
| 2014/0236112 A1 | 8/2014 | Von Wolff et al. | |
| 2014/0308867 A1 | 10/2014 | Van Emmerick et al. | |
| 2015/0320605 A1 | 11/2015 | Pigg et al. | |
| 2016/0030250 A1* | 2/2016 | Caneppele | A61F 13/0008 602/56 |
| 2016/0271291 A1 | 9/2016 | Mansour et al. | |
| 2018/0168871 A1 | 6/2018 | Abelbeck | |
| 2018/0208809 A1 | 7/2018 | Davis et al. | |
| 2018/0289560 A1 | 10/2018 | Caneppele et al. | |
| 2018/0355130 A1 | 12/2018 | Mansour et al. | |
| 2019/0099294 A1 | 4/2019 | Cettina et al. | |
| 2019/0099295 A1 | 4/2019 | Cettina et al. | |
| 2019/0099296 A1 | 4/2019 | Cettina et al. | |

FOREIGN PATENT DOCUMENTS

| | | |
|---|---|---|
| EP | 1075939 A1 | 2/2001 |
| EP | 1400251 A1 | 3/2004 |
| GB | 2308308 A | 6/1997 |
| WO | WO 1999/47590 A | 9/1999 |
| WO | WO 2008/019310 A1 | 2/2008 |

OTHER PUBLICATIONS

European Search Report; Appln. No. 18197737.2-1102; dated May 28, 2019.
"Polymer Properties Database". https://polymerdatabase.com/Films/TPU%20Films.html. (Year: 2015).
"Polyethylene Thermoplastic Characteristics", https://dielectricmfg.com/knolwedge-base/polethylene/. (Year: 2019).

* cited by examiner

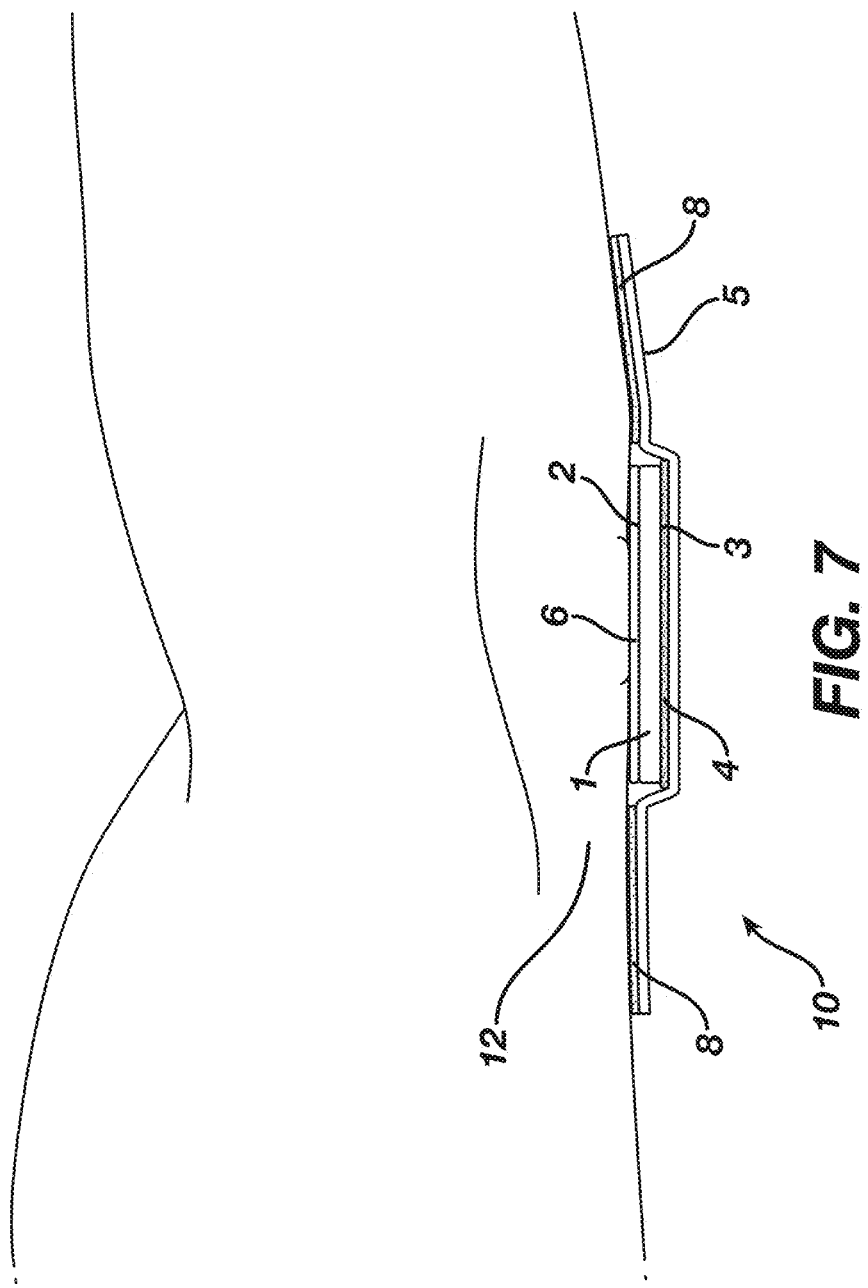

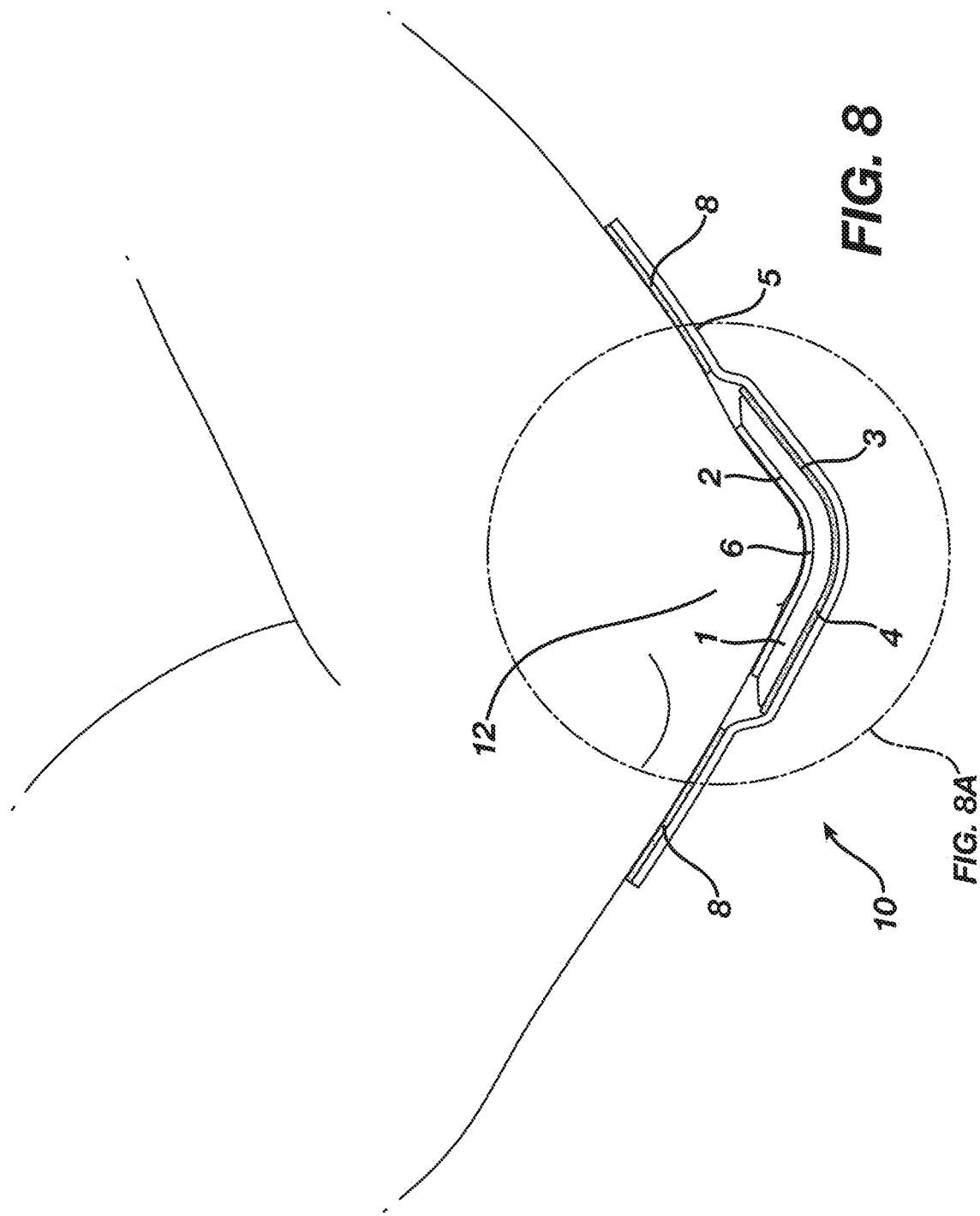

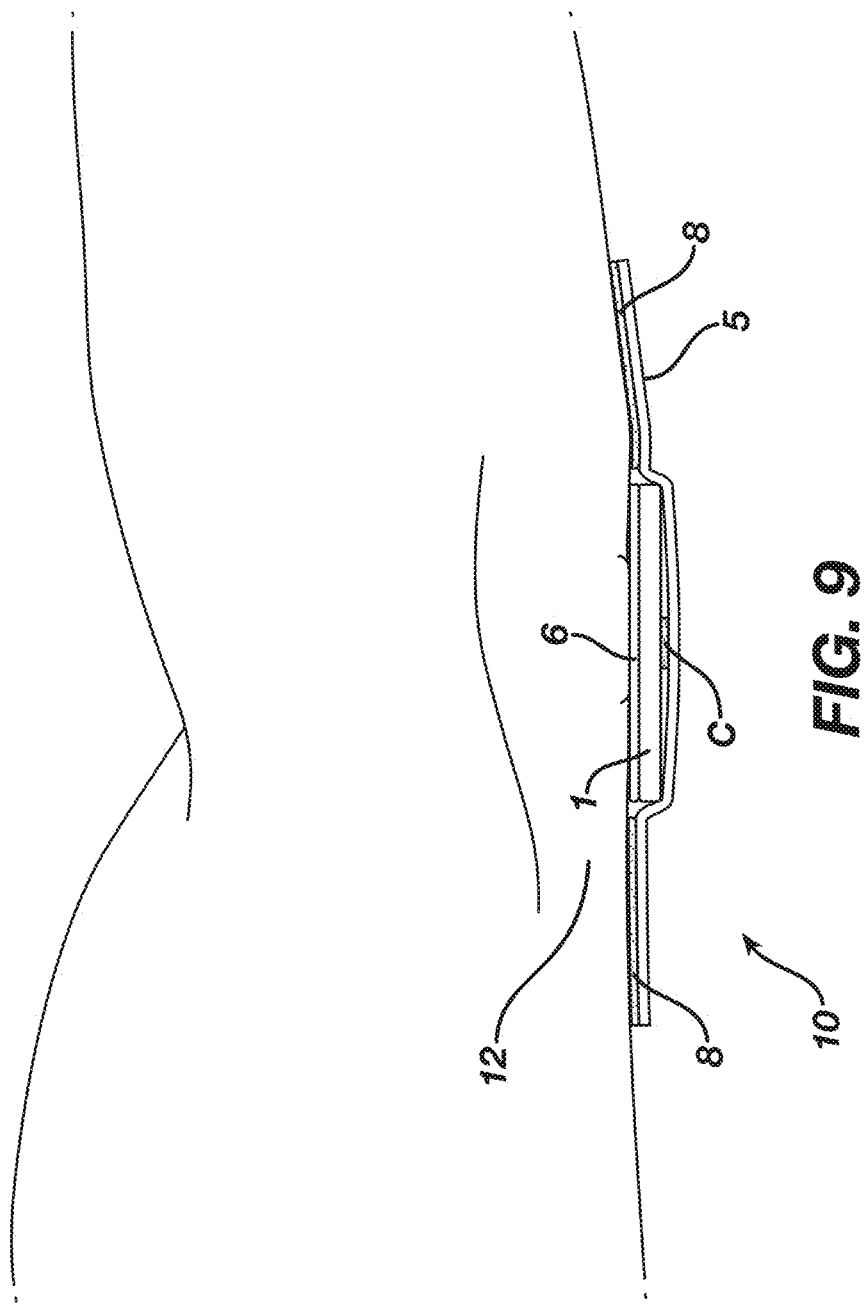

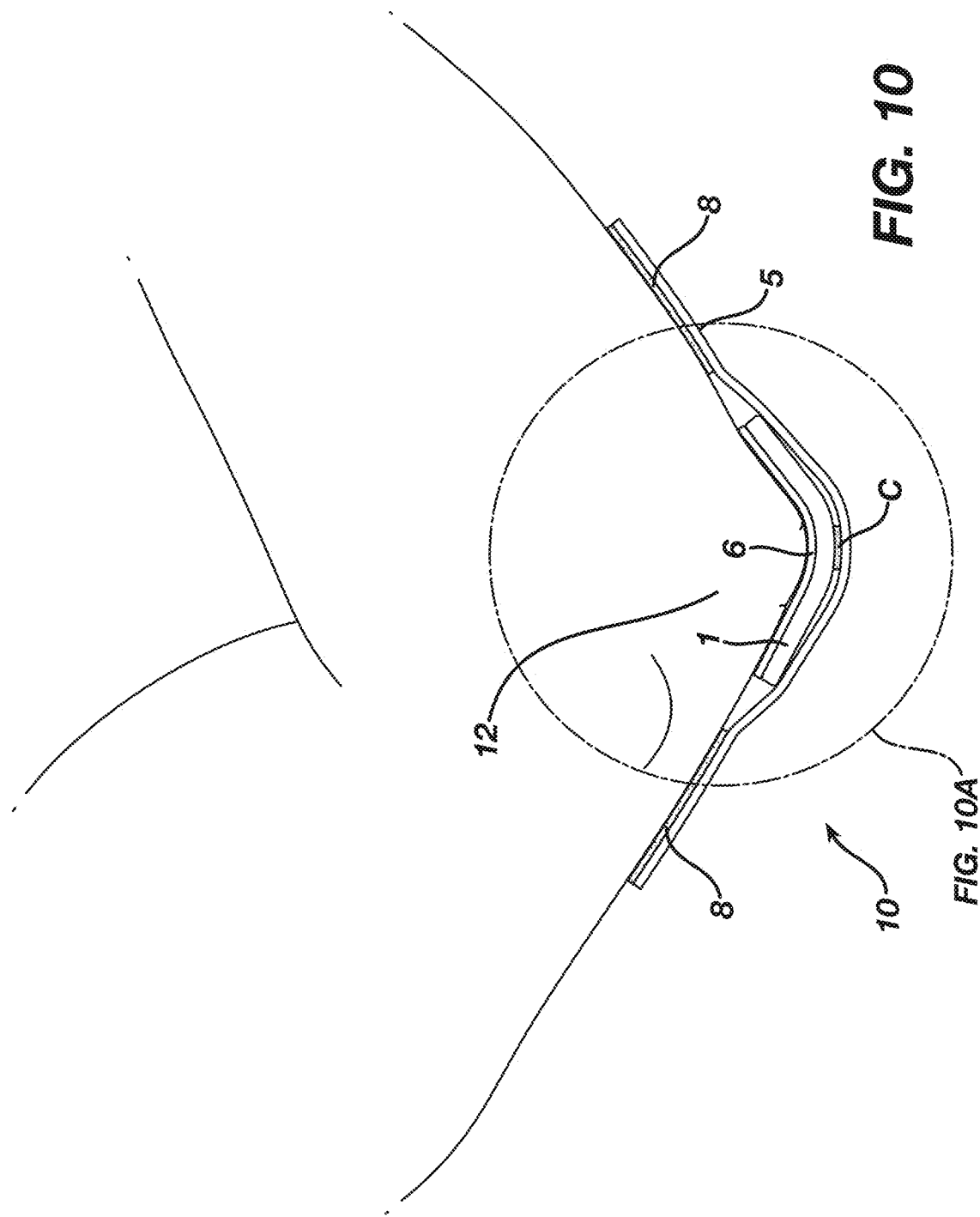

# EXTENSIBLE DRESSINGS

CROSS-REFERENCE TO RELATED APPLICATION

The present application claims the benefit of the earlier filing dates of U.S. provisional patent application 62/565,604, filed Sep. 29, 2017 and U.S. provisional patent application 62/576,210, filed, Oct. 24, 2017, the entirety of each such application is hereby incorporated by reference herein as if fully set forth herein.

FIELD OF THE INVENTION

The present invention relates to dressings such as bandages improved extensibility. The present invention further relates to dressings comprising an absorbent body and backing layer having improved extensibility.

BACKGROUND OF THE INVENTION

Dressings such as bandages for applying to and/or covering the skin have been known for some time. Such dressings have gained wide acceptance for closing minor wounds, protecting minor wounds and/or covering abrasions. In some instances, microporous or breathable, bandages have been developed and are used either to cover minor wounds (including wounds that have been partially healed).

While such dressings have been greatly improved over the years in that, for example, they have incorporated microporous materials allowing the wound to breath and permitting water vapor to escape from the wound, hence, reducing chances of wound maceration, there remains a need for dressings which improves extensibility. Accordingly, the wound dressing assembly of the present invention providing such improved extensibility, comprising an absorbent body and a backing layer attached to the absorbent body by discreet regions of positioning adhesive and/or wherein the absorbent body has an elastic modulus less than or equal to the elastic modulus of the backing layer. In certain embodiments, the wound dressing assembly further comprises a wound contacting layer.

It is, therefore, an aspect of the present invention to provide wound dressing assemblies that may be used to cover, protect wounds and facilitate wound healing. It is also an aspect of the present invention to provide a wound dressing assembly comprising an absorbent body and a backing layer having improved extensibility. It is a further aspect of the present invention to provide a wound dressing assembly comprising an absorbent body and a backing layer attached to the absorbent body by a discreet directional region(s) of positioning adhesive. It is a still further aspect of the present invention to provide a wound dressing assembly comprising an absorbent body and a backing layer wherein the absorbent body has an elastic modulus less than or equal to the elastic modulus of the backing layer. Other aspects of the present invention will be readily apparent from the ensuing description and claims.

SUMMARY OF THE INVENTION

In one embodiment, the present invention relates to a wound dressing assembly comprising:

a. an extensible absorbent body having a longitudinally extending center line, a transversely extending centerline and a periphery, the absorbent body, having a first surface and a second surface, the second surface being opposite the first surface;

b. a positioning adhesive contacting at least a portion of the second surface of the absorbent body;

c. an extensible backing layer adhered to the second surface of the absorbent body by the positioning adhesive such that directional extension of the backing layer causes a corresponding directional extension of the second surface of the absorbent body; and d. a wound contacting layer which is less extensible than the absorbent body, the wound contacting layer disposed on the first surface of the absorbent body such that the second surface of the absorbent body extends upon corresponding extension of the backing layer.

In another embodiment, the present invention relates to a wound dressing assembly comprising:

a. an extensible absorbent body having a longitudinally extending center line, a transversely extending centerline and a periphery, the absorbent body, having a first surface, a second surface and an elastic modulus, the second surface being opposite the first surface;

b. a positioning adhesive contacting at least a portion of the second surface of the absorbent body;

c. a backing layer having an elastic modulus, the backing layer adhered to the second surface of the absorbent body by the positioning adhesive wherein the elastic modulus of the absorbent body is equal to or lower than the elastic modulus of the backing layer.

In a further embodiment, the present invention relates to a wound dressing assembly comprising:

a. an absorbent body having a longitudinally extending centerline, transversely extending centerline and a periphery, the absorbent body, having a first surface and a second surface, the second surface being opposite the first surface, the second surface having;

b. an adhesive contacting the second surface of the absorbent body so as to form a region of positioning adhesive at the center of the second surface of the absorbent body, the region of positioning adhesive having a periphery;

c. a backing layer adhered to the second surface of the absorbent body by the region of positioning adhesive, the backing layer having an inner zone at least partially surrounded by an outer zone, such that the periphery of the region of positioning adhesive defines an inner boundary of a surface area of the backing layer, such surface area of the backing layer extending from the periphery of the region of positioning adhesive in a direction away from periphery of the region of positioning adhesive, beyond at least a portion of the periphery of the absorbent body 1, to the outer zone of the backing layer, such surface area being free of or substantially free of adhesive.

In a still further embodiment, the present invention relates to a wound dressing assembly comprising:

a. an absorbent body having a longitudinally extending centerline, transversely extending centerline and a periphery, the absorbent body, having a first surface and a second surface, the second surface being opposite the first surface, the second surface having:

b. an adhesive contacting the second surface of the absorbent body so as to form a region of positioning adhesive extending substantially along the transversely extending centerline, c. a backing layer adhered to the second surface of the absorbent body by the region of positioning adhesive, the backing layer having an inner zone at least partially surrounded by an outer zone.

wherein the region of positioning adhesive has a first side and a second side, opposite the first side, such that when the region of positioning adhesive contacts the backing layer:
  i. the first side defines an end of a first surface area of the backing layer extending from the first side, beyond the periphery of the absorbent body, to the outer zone of the backing layer in the direction of the longitudinally extending centerline; and
  ii. the second side defines an end of a second surface area of the backing layer extending from the second side, beyond the periphery of the absorbent body, to the outer zone of the backing layer in the direction of the longitudinally extending centerline and opposite the direction of the first surface area, the first and second surface areas being substantially free of adhesive.

BRIEF DESCRIPTION OF THE DRAWINGS

An embodiment of this invention will now be described in greater detail, by way of illustration only, with reference to the accompanying drawings, in which:

FIG. 7 is a side view of the embodiment of the wound dressing assembly 10 shown in FIGS. 1-3 applied to skin 12 and showing the wound-contacting layer 6, absorbent body 1, positioning adhesive 4 and backing layer 5 prior to stretching of backing layer 5.

FIG. 8 is a side view of the embodiment of the wound dressing assembly 10 shown in FIGS. 1-3 applied to skin 12 and showing the wound-contacting layer 6, absorbent body 1, positioning adhesive 4 and backing layer 5 after stretching of backing layer 5.

FIG. 9 is a side view of the embodiment of the wound dressing assembly 10 shown in FIGS. 4-5 applied to skin 12 and showing the absorbent body 1, positioning adhesive region C and backing layer 5 prior to stretching of backing layer 5.

FIG. 10 is a side view of the embodiment of the wound dressing assembly 10 shown in FIGS. 4-5 applied to skin 12 and showing the absorbent body 1, positioning adhesive region C and backing layer 5 after stretching of backing layer 5.

DETAILED DESCRIPTION OF THE INVENTION

The dressing of the present invention can comprise, consist of, or consist essentially of the essential elements and limitations of the invention described herein, as well any of the additional or optional features, components, or limitations described herein.

The term "comprising" (and its grammatical variations) as used herein is used in the inclusive sense of (and, interchangeably with the terms) "having" or "including" and not in the exclusive sense of "consisting only of." The terms "a" and "the" as used herein are understood to encompass the plural as well as the singular.

As used herein, terms "skin" and "tissue" are interchangeable and refer to mammalian skin.

All documents incorporated herein by reference, by portion or in their entirety, are only incorporated herein to the extent that they are not inconsistent with this specification.

In certain embodiments, the present invention as disclosed herein may be practiced in the absence of any component, element (or group of components or elements) or method step which is not specifically disclosed herein.

Dressing Assembly

Absorbent Body

Figure 1:
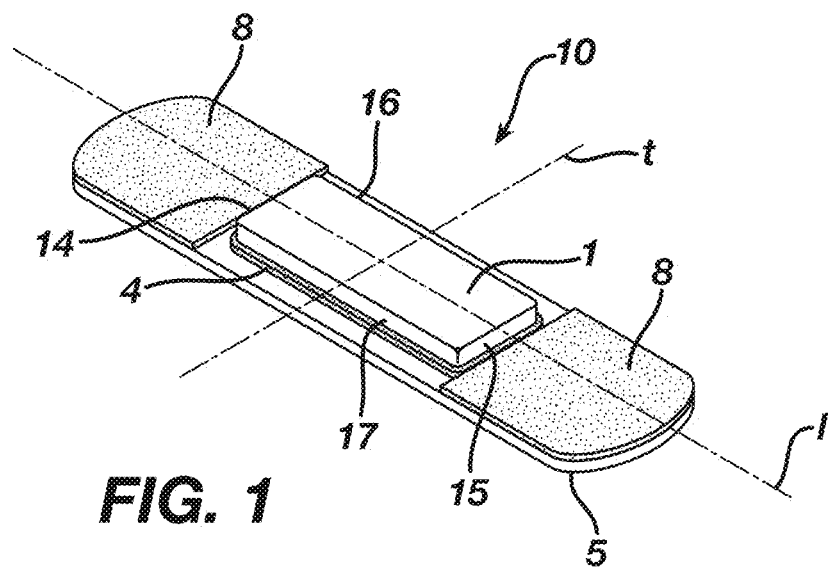
FIG. 1 is a perspective view of an embodiment of a wound dressing assembly 10.
Figure 2:
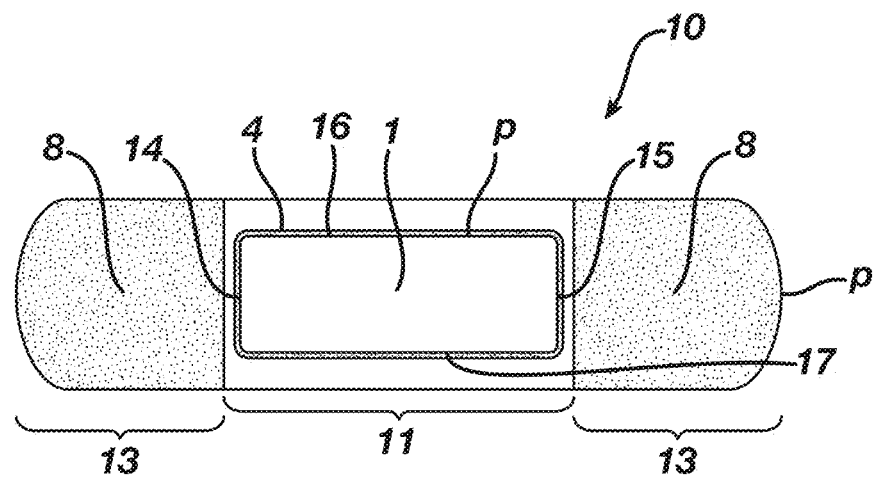
FIG. 2 is a top plan view of the embodiment of the wound dressing assembly 10 shown in FIG. 1.
Figure 3:
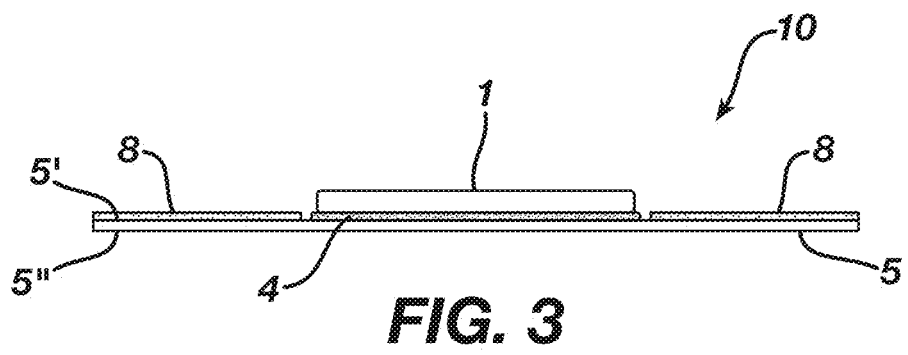
FIG. 3 is a side view of the embodiment of the wound dressing assembly 10 shown in FIG. 1.

In certain embodiments, dressing assembly 10 of the present invention comprises an absorbent body 1 having an elastic modulus (calculated as indicated below). As shown in FIGS. 1 and 3, the absorbent body 1 has a longitudinally extending center line l and transversely extending centerline t, the absorbent body 1 having a first longitudinal edge 14, a second longitudinal edge 15, a first transverse edge 16, and a second transverse edge 17 each, collectively or individually, defining a periphery p. The absorbent body 1 also has a first surface 2 which is a wound facing surface and a second surface 3 (the second surface 3 located opposite the first surface 2).

In certain embodiments, the absorbent body 1 comprises any material that is conformable, non-irritating to the wearer's skin, and capable of absorbing and retaining liquids. The absorbent body 1 may be, or in the form of, a single layer or multilayer material, wherein if it is a multilayer material each layer may be of the same material or of different materials.

Examples of materials that would be suitable for the absorbent body 1 includes or comprises creped cellulose wadding; melt blown polymers; chemically stiffened, modified or cross-linked cellulosic fibers; tissue; absorbent foams; absorbent sponges; superabsorbent polymers; absorbent gelling materials; or any other known absorbent material or combinations of any such materials. In certain embodiments, the absorbent body 1 can be a web produced by electrospinning; a nonwoven (i.e., a natural or synthetic nonwoven including fibrous and nonfibrous nonwovens); a woven; a film (e.g., a formed film); a batting; spunbond; spunlace; hydroentangled; carded; needle-punched; wetlaid or any other suitable material. A more detailed description of the materials useful in forming the absorbent body 1 can be found in U.S. Pat. No. 9,445,951B2 and US Patent Publication 20140308867A1, each of which patent documents is herein incorporated by reference in its entirety. The absorbent body 1 may further comprise minor amounts (typically less than 10%) of non-liquid absorbent materials, such as adhesives, waxes, oils, antimicrobials, active ointments, and the like, for example.

In one embodiment, the absorbent body 1 is or comprises a foam material, optionally an open-cell foam. The foam may include a synthetic polymer that is adapted to form a conformable open-cell foam that absorbs the wound exudate. Examples of suitable materials for the foams include synthetic organic polymers including (or selected from), but not limited to: The polymeric foams can be made of, or comprises, a polymer comprising one or more types of monomers (e.g., copolymers) or mixtures (e.g., blends) of polymers. Examples of foam materials are described in the book entitled "Flexible Polyurethane Foams", Dow Polyurethanes, editors R. Herrington and K. Hock, 1997.

The foams can be of a wide range of thicknesses; from about 0.5 mm or 1 mm to about 3 mm or 10 mm thick. Furthermore, they can include one or more layers tailored to have the desired properties. These layers can be directly bonded to each other or bonded together with adhesive layers. Optionally, disposed between these layers can be one or more layers of polymeric netting or nonwoven, woven, or knit webs for enhancing the physical integrity of the foam.

In another embodiment, the absorbent body 1 comprises superabsorbing particles or fibers contained within a porous pouch. Examples include superabsorbent fibrous webs that are available from National Nonwovens, Cincinnati, Ohio or sachets containing superabsorbent material such as Sorbion Sachet S available from Sorbion AG, Senden, Germany. Super absorbing particles are also available as AQUA KEEP Superabsorbent powder available from Sumitomo Seika Chemicals Co., Ltd. (Osaka, Japan) and HySorb® Superabsorbent powder available from BASF Corporation (Portsmouth, Va.).

One example of a suitable absorbent body 1 is found in Delstar's (Del.) PET nonwoven pad. Other examples include Delstar's polyolefin nonwovens and blends of rayon and polyester or rayon and polyolefin. Suitable constructions for the absorbent body are disclosed in U.S. Pat. Nos. 6,838, 589; 7,030,288; and 7,612,248, the disclosure of which patents are herein incorporated by reference.

In other embodiments, the absorbent body 1 comprises hydrocolloids.

The hydrocolloid element used may be any substance that has a good performance in this utilization, as for example, sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof, among others.

Hydrocolloids, just as sodium carboxymethylcellulose and pectin, among others, are agents that form gels as soon as they come into contact with the bodily fluids from the wound. When used in adhesive bandages, these hydrocolloids may be combined with elastomers and/or adhesives. In certain embodiments, the absorbent body 1 comprising such hydrocolloids should provide a humid environment (but without saturation), which environment is a situation suitable for facilitating healing.

Positioning Adhesive

The second surface 3 of absorbent body 1 secured to a backing layer 5 by a positioning adhesive 4.

The positioning adhesive 4 is typically a pressure sensitive positioning adhesive, and, in some embodiments, can be a pressure sensitive adhesive used for application to the skin (i.e., causing minimal to no adverse skin effects and easily removed from skin with minimal to no discomfort). Accordingly, in certain embodiments, the positioning adhesive 4 can be the same as skin contacting adhesive 8 (described below, including specific examples of useful skin contacting adhesives). Other useful positioning adhesives are described in U.S. Pat. No. RE 24,906; U.S. Pat. No. 4,737,410 (Example 31); and U.S. Pat. Nos. 3,389,827, 4,112,213, 4,310,509, and 4,323,557, each of which the patents are hereby incorporated by reference.

In certain embodiments, the positioning adhesive 4 is disposed on or contacts the second surface 3 of absorbent body 1 so as to form a continuous or discontinuous layer or surface area of positioning adhesive 4.

Figure 6:
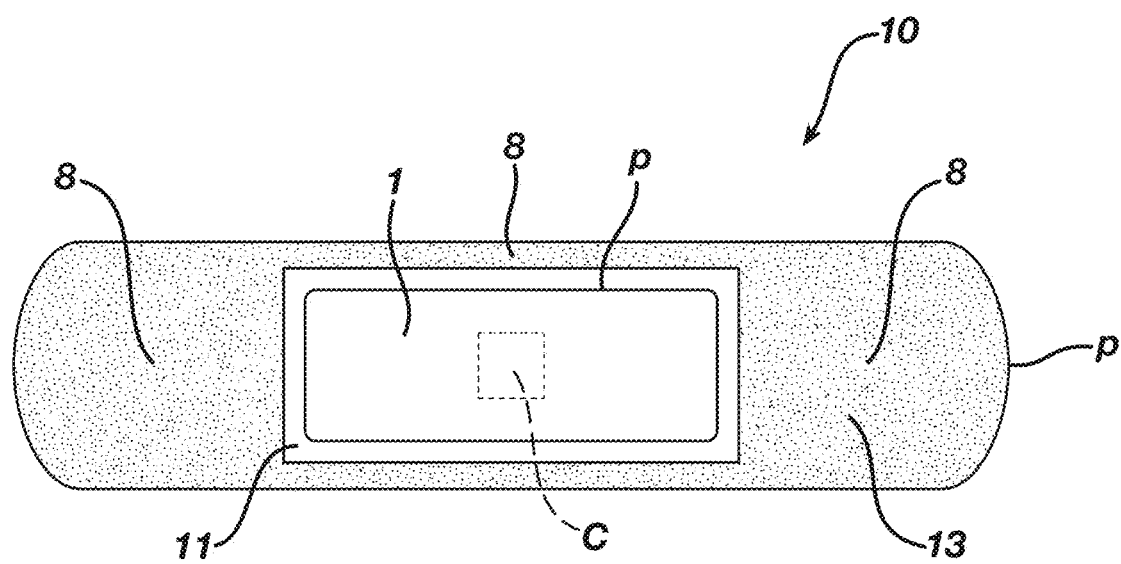
FIG. 6 is a top plan view of another embodiment of the wound dressing assembly 10 of the present invention, showing the positioning adhesive region C in a distinct centralized region on second surface 3 through the absorbent body 1.

In one embodiment, as shown in FIG. 6, the positioning adhesive 4 is disposed on or contacts the second surface 3 of absorbent body 1 so as to form a region C of the positioning adhesive 4 at, or near, the center of the second surface 3 of the absorbent body 1 (i.e., where the longitudinally extending center line/and transversely extending centerline t intersect), the region C of positioning adhesive 4 having a periphery c.

Figure 4:
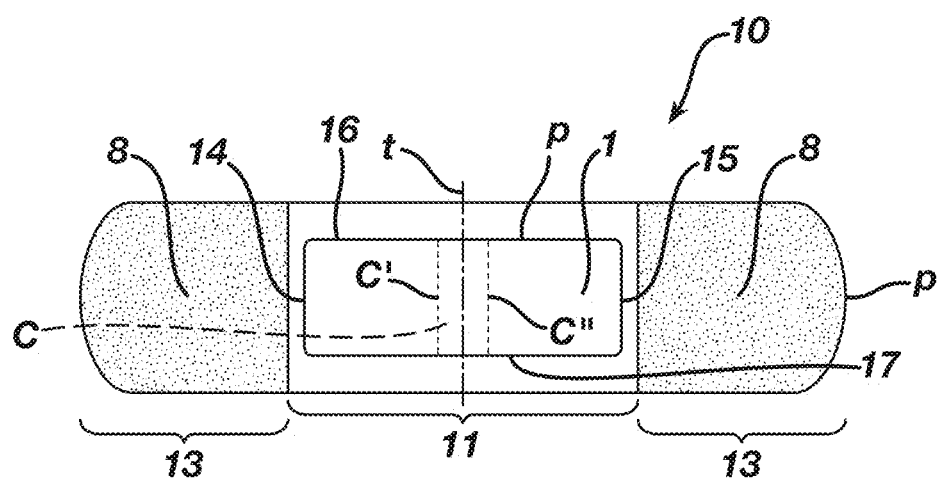
FIG. 4 is a top plan view of another embodiment of the wound dressing assembly 10 of the present invention, showing position of positioning adhesive region C through the absorbent body 1.
Figure 5:
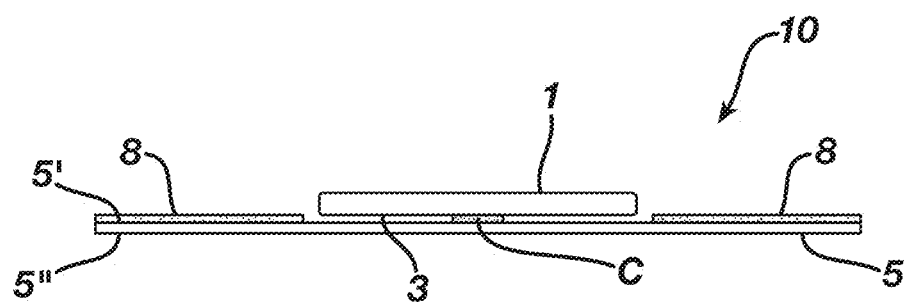
FIG. 5 is a side view of the embodiment of the wound dressing assembly 10 shown in FIG. 4, showing positioning adhesive region C contacting second surface 3 of the absorbent body 1 and backing layer 5.

In another embodiment, as shown in FIGS. 4-5, the positioning adhesive 4 is disposed on or contacts the second surface 3 of absorbent body 1, in the center of the second surface 3 of the absorbent body 1 where a longitudinally extending center line l and transversely extending centerline t intersect, so as to form a region C of positioning adhesive 4, which region C can further extends directionally substantially along the transversely extending centerline t, the region C of positioning adhesive 4 forming a first side C' and second side C", opposite the first side C'.

The phrase "substantially along" with respect to positioning adhesive region C relative to the transversely extending centerline t means that the positioning adhesive region can be of any directional pattern or shape, including being aligned with, diagonal to or intersecting (such as in the case of a sinusoidally intersecting pattern) the transversely extending centerline t, so long as the positioning adhesive region extends in the general direction of the given centerline. Additionally, a first side C' and second side C" can have any linear pattern, and have the same or different such pattern(s).

Backing Layer

The dressing assembly 10 further comprises a backing layer 5 having a front surface 5' and back surface 5" (the back surface 5" located opposite the front surface 5'), the backing layer 5 having an outer zone 13, inner zone 11 and a periphery P, the inner zone 11 either partially (as in FIG. 4) or completely (as in FIG. 6) surrounded by outer zone 13. The front surface 5' of the backing layer 5 is adhered to the second surface 3 of the absorbent body 1 by the positioning adhesive 4 (or region C of positioning adhesive 4) and, in certain embodiments, such that the absorbent body 1 is positioned within the inner zone 11. In certain embodiments, the front surface 5' of the backing layer 5 is adhered to the second surface 3 of the absorbent body 1 by the positioning adhesive 4 such that directional extension of the backing layer 5 causes a corresponding directional extension of the second surface 3 of the absorbent body 1. The backing layer 5 can comprise a single or multiple layers (or backing layers).

In certain embodiments, the edge of periphery P of the backing layer 5 extends beyond the edges of, at least, a portion of the periphery p of the absorbent body 1—so that backing layer 5, at least partially, covers and, at least partially, extends beyond the absorbent layer 1 to adhere to a user's skin. In certain embodiments, the edge of the entire periphery P of the backing layer 5 extends beyond the entire edge of periphery p of the absorbent body 1—so that backing layer 5 fully covers and fully extends beyond the absorbent body 1 to adhere to a user's skin.

In certain embodiments, the positioning adhesive 4 contacts the front surface 5' of backing layer 5 to adhere the front surface 5' of backing layer 5 to the second surface 3 of absorbent body 1.

In certain embodiments, the region C of positioning adhesive 4 contacts both i) the second surface 3 of the absorbent body 1 at, or near, its center (i.e., where a longitudinally extending center line l and transversely extending centerline t intersect) and ii) the front surface 5' of the backing layer 5 such that the front surface 5' of backing layer 5 adheres to the second surface 3 of absorbent body 1 and forms a periphery c defining an inner boundary of a surface area of backing layer 5, such surface area of backing layer 5 extending from periphery c in a direction away from periphery c, beyond at least a portion of the periphery p of the absorbent body 1, to the outer zone 13 of the backing layer 5 as shown in FIG. 6. Such surface area of backing layer 5 is free of or substantially free of adhesive.

In one embodiment, as shown in FIGS. 4-5, the region C of positioning adhesive 4, as described above, further extends directionally substantially along the transversely extending centerline t, the region C contacting the front surface 5' backing layer 5 to adhere the front surface 5' of backing layer 5 to the second surface 3 of absorbent body 1 such that:

i) the first side C' defines an end of a first surface area of the backing layer extending from the first side C', beyond at least a portion of the periphery p of the absorbent body 1, to the outer zone 13 of the backing layer 5 in the direction of the longitudinally extending centerline l, first surface area bounded by the outer zone 13; and ii) the second side C" defines an end of a second surface area of the backing layer extending from the second side, beyond the periphery of the absorbent body, to the outer zone 13 of the backing layer 5 in the direction of the longitudinally extending centerline and opposite the direction of the first surface area, second surface area bounded by the outer zone 13, the first and second surface areas being substantially free of adhesive.

As described herein with respect to surface areas of the backing layer 5 which are substantially free of adhesive, the term "substantially free of adhesive" means that there is less than 20%, optionally, less than 15%, optionally less than 5%, optionally less 2.5% or optionally zero percent of the described surface area contacts or has disposed thereon it any adhesive or compound having adhesive properties.

Figure 10A:
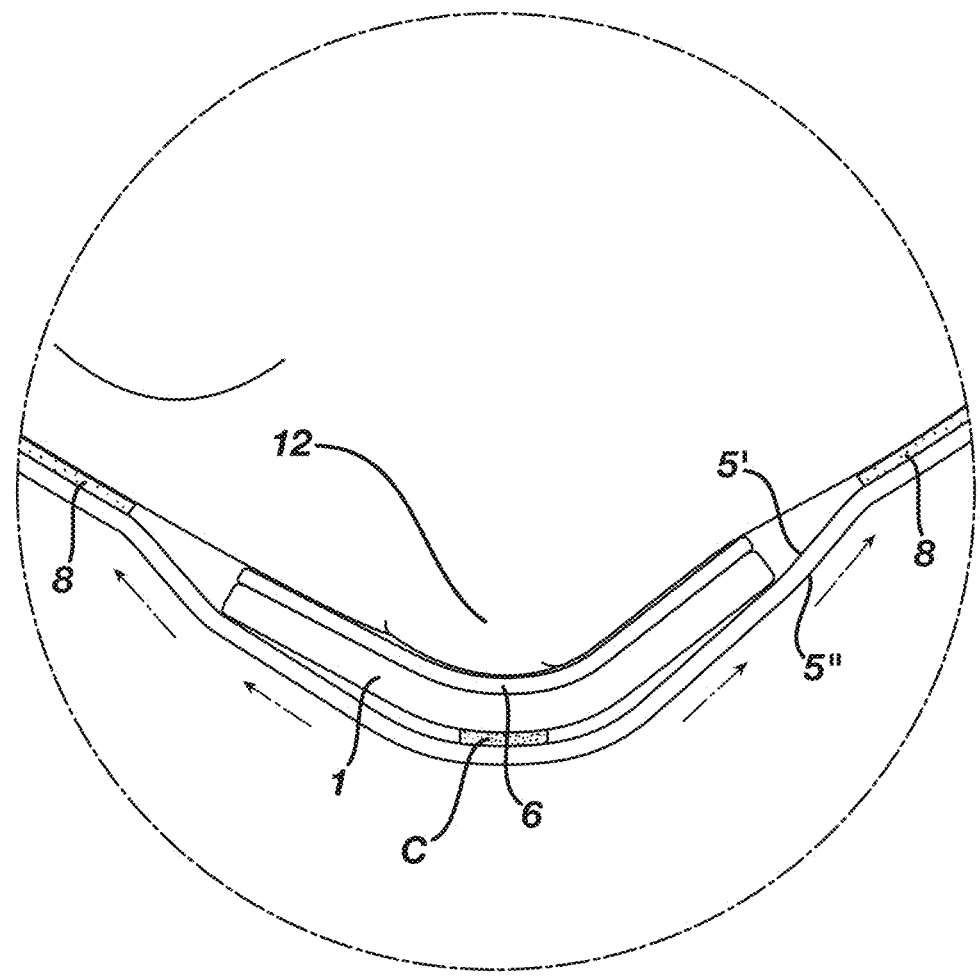
FIG. 10A is a magnification of encircled FIG. 10A in FIG. 10 showing that any stretching of backing layer 5 has minimal affect on the absorbent body 1 due to reduced contact between the absorbent body 1 and the positioning adhesive region C.
Figure 11:
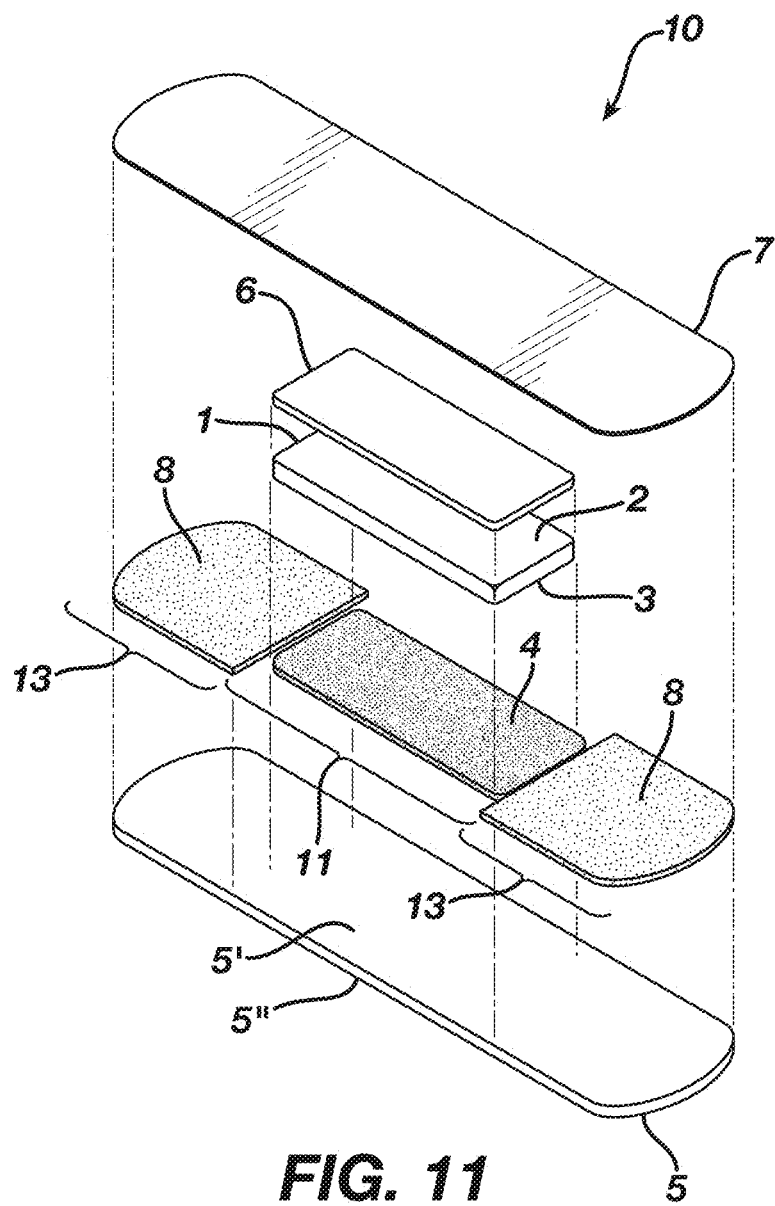
FIG. 11 is an exploded view of an embodiment of the wound dressing assembly 10 of the present invention showing absorbent body 1, positioning adhesive 4, and backing layer 5, and, optional, wound-contacting layer 6 and release liner 7.

Without be limited by theory, as shown in FIGS. 9-10A, it is believed that placement of the positioning adhesive as a region of positioning adhesive centrally (e.g., in the center of) or extending substantially along the transversely extending centerline t, relative to the second surface 3 of absorbent body 1, as explained above, minimizes any movement or stretch of the absorbent body 1 due to movement or stretch of the attached backing layer 5.

In certain embodiments, the elastic modulus of the absorbent body 1 is equal to or lower than the elastic modulus of backing layer 5, or the load/force needed to extend the absorbent body 1 a given percent change in length which is equal to or lower than the load/force needed to extend the backing layer the same percent change in length. The "elastic modulus" (e.g., of the absorbent body 1 and/or the backing layer 5), as used herein, is calculated as follows, upon obtaining "stretch" measurements in accordance with a modified version of ASTM D882, Standard Test Method for Tensile Properties of Thin Plastic Sheeting (ASTM International, West Conshohocken, Pa., 2016):

ASTM D882-9 originally calls for a grip distance of 250 mm and an initial strain rate of 0.1 mm/mm*min. However, for purposes of obtaining measurements to calculate elastic modulus materials of the present invention, a grip distance of 50 mm and an initial strain rate of 10 mm/mm*min is used instead. The modified dimensions and rates a are the same as those used for obtaining the other tensile properties (e.g., tensile breaking strength or elongation at break) of thin plastic films. Once a load-extension curve is generated as describe in ASTM D882, the elastic modulus is determined by drawing a tangent to the initial linear portion of the load-extension curve, selecting any point on this tangent and dividing the tensile stress by the corresponding strain.

An example of wound dressing assembly 10 where the elastic modulus of the absorbent body 1 is equal to or lower than the elastic modulus of backing layer 5 can be seen where: a) the absorbent body 1 is a nonwoven substrate having a basis weight of from about 50 gsm to about 200 gsm, optionally about 100 gsm and formed from (e.g., spun bonded) filaments (or fibers) of polyurethane having a filament/fiber diameter of from about 50 nm to about 50000 nm, optionally from about 50 nm to about 20000 nm, optionally from about 100 nm to about 10000 nm, optionally from about 500 nm to about 3000 nm; and b) the backing layer 5 is selected from i) a 25 μm to 50 μm thick polyurethane film layer; or ii) a 50 μm to 300 μm thick a melt blown polyurethane nonwoven.

An example of the nonwoven polyurethane, nano-filament substrate useful for absorbent body 1 is Nanosan® Sorb/100, supplied by SNS Nano Fibre technology, Hudson, Ohio. Nanosan® Sorb/100. The elastic modulus of Nanosan® Sorb/100 was measured to be 0.2 MPa (or about 0.2 MPa). A more detailed discussion of useful such nanofiber nonwovens can be found in U.S. Pat. No. 4,043,331, which patent is herein incorporated by reference in its entirety.

The elastic modulus of the melt blown polyurethane nonwoven backing layer 5 was measured to be 2.2 MPa (or about 2.2 MPa). The wound assembly having an absorbent body 1 of elastic modulus equal to or lower than the elastic modulus of backing layer 5, reduces or prevents restriction in extensibility of backing layer 5 upon adherence to the absorbent body 1.

In certain embodiments, the elastic modulus of the backing layer 5 can range from about 1 MPa to about 50 MPa, or optionally from about 1.5 MPa to about 6 MPa.

In certain embodiments, the backing layer 5 may include a liquid-impervious, moisture-vapor permeable polymeric film, although it can, optionally, include a variety of other materials, which are preferably used in combination with a liquid-impervious, moisture-vapor permeable polymeric film. The liquid-impervious, moisture-vapor permeable polymeric film is a conformable organic polymeric material that preferably retains its structural integrity in a moist environment. As used herein, "conformable" films are those that conform to a surface, even upon movement of the surface, as with the surface of a body part. Suitable films have a composition and thickness that allow for the passage of moisture vapor through them. The film aids in the regulation of water vapor loss from the wound area beneath the dressing. The film also acts as a barrier to both bacteria and to liquid water or other liquids.

The moisture-vapor permeable polymeric films can be of a wide range of thicknesses. Preferably, they are from about 10 microns or 12 microns to 75 microns or 250 microns thick. Furthermore, they can include one or more layers tailored to have the desired properties. These layers can be coextruded and/or bonded together with a suitable adhesive, for example, as long as the overall properties of the film and article, as described herein, are met.

Examples of suitable materials for the liquid-impervious, moisture-vapor permeable polymeric films include synthetic organic polymers including, but not limited to: polyurethanes commercially available from B.F. Goodrich, Cleveland, Ohio, under the trade designation ESTANE, including ESTANE 58237 and ESTANE 58245; poly-amide block copolymers commercially available from Arkema, King of Prussia, Pa., under the trade designation PEBAX, including PEBAX MV 1074; polyester block copolymers commercially available from DuPont, Wilmington, Del., under the trade designation HYTREL. The polymeric films can be made of one or more types of monomers (e.g., copolymers) or mixtures (e.g., blends) of polymers. An example material is thermoplastic polymers (e.g., those that soften when exposed to heat and return to their original condition when cooled), such as thermoplastic polyurethane.

Backing layers of backing layer 5 of the dressing assemblies 10 of the present invention can, optionally, be other breathable materials including, for example, nonwoven, woven, and knit webs, porous films (e.g., provided by perforations or microporous structure), or other known backings. One such nonwoven web is a melt processed polyurethane (such as that available under the trade designation MORTHANE PS-440 from Morton International, Seabrook, N.H.), or hydroentangled nonwoven polyester or rayon-polyester webs (such as those available under the trade designation SONTARA 8010 or SONTARA 8411 from DuPont, Wilmington, Del.).

The backing layers of backing layer 5 may be a combination of a liquid-impervious, moisture-vapor permeable polymeric film and a moisture-vapor permeable nonwoven, woven, or knit web, or a porous film that can, among other advantages, impart enhanced structural integrity and improved aesthetics to the dressings of the present invention. The layers within (or forming) the backing layers are preferably bonded together using a suitable adhesive layer, for example, that can be continuous or discontinuous (e.g., such as that produced with a pattern-coated adhesive layer), although other means of bonding can be used including thermomechanical bonding, such as thermal bonding or ultrasonic welding.

In certain embodiments, the front surface backing layer 5 may further contact or have disposed on it a skin contacting adhesive 8 for attachment of the wound assembly 10 to the skin of a user. In certain embodiments, the skin contacting adhesive 8 contacts or is disposed on the front surface 5' of the backing layer 5 within outer zone 13. In general, any of a variety of pressure-sensitive adhesives can be utilized as the skin contacting adhesive 8. In particular, pressure-sensitive adhesives that are biocompatible with human skin are typically utilized. In some embodiments, the skin contacting adhesive 8 may also be either generally water soluble or generally insoluble, or dispersible in an aqueous environment. In certain embodiments, the skin contacting adhesive 8 may be either generally insoluble or dispersible in an aqueous environment. Suitable examples include, for instance, commercially available dispersible pressure-sensitive adhesive is sold under the trade name of HL-9415-X and is available from H.B. Fuller Company. Another suitable adhesive includes about 10-75% by weight of a polyalkyloxazoline polymer, 10-75% by weight of a functional diluent comprising a hydroxy compound or a carboxylic acid compound, and 5-50% by weight of a tackifier.

Optional Components

Wound Contacting Layer

In certain embodiments, a wound contacting layer 6 contacts the first surface 2 of the absorbent body 1. Examples of such wound-contacting layers 6 include polymeric netting and porous (e.g., perforated) films, or other conventional materials that prevent the dressing from sticking to the wound while allowing penetration of fluids into the absorbent body 1. In certain embodiments, the wound-contacting layer 6 contacts the absorbent body 1 by direct bonding to the absorbent body 1 (e.g., cast or thermomechanical bonding), or by using an adhesive layer.

One example of a suitable wound contacting layer are high density polyethylene (HDPE) nets which are available from Delnet Technologies (Del.) under Delnet® AC530WHT net.

Figure 8A:
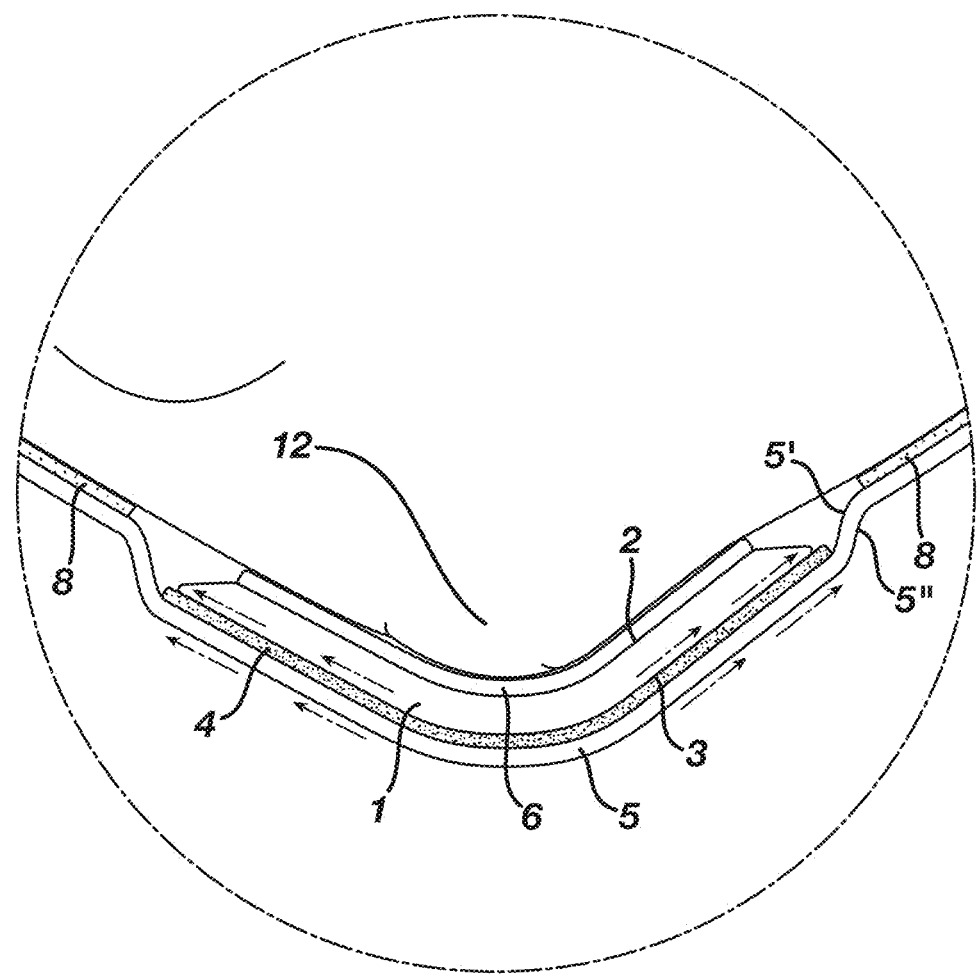
FIG. 8A is a magnification of encircled FIG. 8A in FIG. 8, showing stretching of second surface 3 of absorbent body 1 upon stretching of backing layer 5 despite restricted movement of first surface 2 of absorbent body 1 due to its adherence to the less extensible wound-contacting layer 6.

In one embodiments, as shown in FIGS. 7-8A, the wound contacting layer 6 may have an elastic modulus which is higher than the elastic modulus of the absorbent body 1 such that the wound contacting layer 6 is less extensible than the absorbent body 1. In such embodiments, the wound contacting layer 6 is adhered onto the first surface 2 of the absorbent body 1 such that the second surface 3 (adhered to front surface 5' of backing layer 5) of the absorbent body 1 extends (or retains/maintains extensibility so as to extend) directionally upon corresponding directional extension of the backing layer 5. Accordingly, the extensibility of the absorbent body 1 is such that upon adhering a wound contacting layer 6 having the above-described properties to the first surface 2 of the absorbent body 1, the second surface 3 (adhered to front surface 5' of backing layer 5) of the absorbent body 1 retains (or maintains) its ability to move or stretch directionally (e.g., in response to corresponding directional movement or stretch in the adhered of backing layer 5 and its front surface 5') despite any restriction in movement or stretch of the first surface 2 of absorbent body 1 due to its adherence to the less extensible wound contacting layer 6.

In certain embodiments, the elastic modulus of absorbent body 1 is 25% less than, optionally 50% less than, optionally 75% less than, or optionally 95% less than the elastic modulus of the wound contacting layer 6.

Release Liner

A release liner 7 may be used to cover any exposed adhesive on the absorbent body 1 or backing layer 5. The release liner 7 may be in the form of unitary layer or segmented portions of a layer. Release liners 7 can be made of kraft papers, polyethylene, polypropylene, polyester, polystyrene (such as high impact polystyrene) or composites of any of these materials. In one embodiment, the release liners 7 are coated with release agents such as fluorochemicals or silicones. For example, U.S. Pat. No. 4,472,480, the disclosure of which is hereby incorporated by reference, describes low surface energy perfluorochemical liners. In one embodiment, the release liners 7 are papers, polyolefin films, or polyester films coated with silicone release materials. Examples of commercially available silicone coated release papers are supplied by Wausau Paper Specialty Products (Rhinelander, Wis.) and Mondi Packaging (Lancaster, Ohio). One suitable release liner is a 60 # per 3000 square feet bleached kraft SC RLSE D11 442-6001 paper liner available from Wausau Paper Specialty Products. Optionally, the release liner 7 may include a tab which facilitates the easy removal of the release liner from the backing layer 5 or absorbent body 1 of the dressing assembly 10.

Although specific embodiments of this invention have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

Embodiments of the Present Invention

1. A wound dressing assembly comprising:
   a. an extensible absorbent body having a longitudinally extending center line, a transversely extending centerline and a periphery, the absorbent body, having a first surface and a second surface, the second surface being opposite the first surface;
   b. a positioning adhesive contacting at least a portion of the second surface of the absorbent body;
   c. an extensible backing layer adhered to the second surface of the absorbent body by the positioning adhesive such that directional extension of the backing layer causes a corresponding directional extension of the second surface of the absorbent body; and
   d. a wound contacting layer which is less extensible than the absorbent body, the wound contacting layer disposed on the first surface of the absorbent body such that the second surface of the absorbent body extends upon corresponding extension of the backing layer.
2. The wound dressing assembly of embodiment 1 wherein the absorbent body is in the form of a single layer or multilayer material.
3. The wound dressing assembly of embodiments 1 and/or 2 wherein the absorbent body comprises creped cellulose wadding; melt blown polymers; chemically stiffened, modified or cross-linked cellulosic fibers; tissue; absorbent foams; absorbent sponges; superabsorbent polymers; absorbent gelling materials; or combinations of such materials.
4. The wound dressing assembly of any one of or combination of embodiments 1 to 3 wherein the absorbent body comprises a web produced by electrospinning; a nonwoven; a woven; a film; a batting; spunbond; spunlace; hydroentangled; carded; needle-punched; wetlaid or any other suitable material.
5. The wound dressing assembly of any one of or combination of embodiments 1 to 4 wherein the absorbent body comprises a foam material.
6. The wound dressing assembly of any one of or combination of embodiments 1 to 5 wherein the foam material comprises a polymer comprising one or more types of monomers or blend of polymers.
7. The wound dressing assembly of any one of or combination of embodiments 1 to 6 wherein the foam material is an open cell foam.
8. The wound dressing assembly of any one of or combination of embodiments 1 to 7 wherein the foam material is an open cell foam synthetic organic polymer selected from polyurethanes, carboxylated butadiene-styrene rubbers, polyesters, polyacrylates or mixtures thereof
9. The wound dressing assembly of any one of or combination of embodiments 1 to 8 wherein the absorbent body comprises hydrocolloids.
10. The wound dressing assembly of any one of or combination of embodiments 1 to 9 wherein the hydrocolloids is selected from sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof and mixtures thereof.
11. The wound dressing assembly of any one of or combination of embodiments 1 to 10 wherein the positioning adhesive contacts the second surface of absorbent body to form a continuous or discontinuous layer or surface area of positioning adhesive
12. The wound dressing assembly of any one of or combination of embodiments 1 to 11 wherein the backing layer has a periphery such that the periphery of the backing layer extends beyond at least a portion of the periphery of the absorbent body.
13. A wound dressing assembly comprising:
    d. an extensible absorbent body having a longitudinally extending center line, a transversely extending centerline and a periphery, the absorbent body, having a first surface, a second surface and an elastic modulus, the second surface being opposite the first surface;
    e. a positioning adhesive contacting at least a portion of the second surface of the absorbent body;
    f. a backing layer having an elastic modulus, the backing layer adhered to the second surface of the absorbent body by the positioning adhesive
    wherein the elastic modulus of the absorbent body is equal to or lower than the elastic modulus of the backing layer.
14. The wound dressing assembly of embodiment 13 wherein the elastic modulus of the backing layer is from about 1 MPa to about 50 MPa.
15. The wound dressing assembly of embodiments 13 and/or 14 wherein the elastic modulus of the backing layer is from about 1.5 MPa to about 6 MPa.
16. The wound dressing assembly of any one of or combination of embodiments 13 to 15 wherein the absorbent body is a nonwoven substrate having a basis weight of from about 50 gsm to about 200 gsm and formed from filaments of polyurethane having a filament diameter of from about 500 nm to about 3000 nm.
17. The wound dressing assembly of any one of or combination of embodiments 13 to 16 wherein the backing layer is selected from i) a 25 μm to 50 μm thick polyurethane film layer; or ii) a 50 μm to 300 μm thick a melt blown polyurethane nonwoven.
18. The wound dressing assembly of any one of or combination of embodiments 13 to 17 wherein the absorbent body is in the form of a single layer or multilayer material.
19. The wound dressing assembly of any one of or combination of embodiments 13 to 18 wherein the absorbent body comprises creped cellulose wadding; melt blown polymers; chemically stiffened, modified or cross-linked cellulosic fibers; tissue; absorbent foams; absorbent sponges; superabsorbent polymers; absorbent gelling materials; or combinations of such materials.
20. The wound dressing assembly of any one of or combination of embodiments 13 to 19 wherein the absorbent body comprises a web produced by electrospinning; a nonwoven; a woven; a film; a batting; spunbond; spunlace; hydroentangled; carded; needle-punched; wetlaid or any other suitable material.
21. The wound dressing assembly of any one of or combination of embodiments 13 to 20 wherein the absorbent body comprises a foam material.
22. The wound dressing assembly of any one of or combination of embodiments 13 to 21 wherein the foam material comprises a polymer comprising one or more types of monomers or blend of polymers.
23. The wound dressing assembly of any one of or combination of embodiments 13 to 22 wherein the foam material is an open cell foam.
24. The wound dressing assembly of any one of or combination of embodiments 13 to 23 wherein the foam material is an open cell foam synthetic organic polymer selected from polyurethanes, carboxylated butadiene-styrene rubbers, polyesters, polyacrylates or mixtures thereof
25. The wound dressing assembly of any one of or combination of embodiments 13 to 24 wherein the absorbent body comprises hydrocolloids.
26. The wound dressing assembly of any one of or combination of embodiments 13 to 25 wherein the hydrocolloids is selected from sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof and mixtures thereof
27. The wound dressing assembly of any one of or combination of embodiments 13 to 26 wherein the position adhesive contacts the second surface of absorbent body to form a continuous or discontinuous layer or surface area of positioning adhesive
28. The wound dressing assembly of any one of or combination of embodiments 13 to 27 wherein the backing layer has a periphery such that the periphery of the backing layer extends beyond at least a portion of the periphery of the absorbent body.
29. A wound dressing assembly comprising:
 b. an absorbent body having a longitudinally extending centerline, transversely extending centerline and a periphery, the absorbent body, having a first surface and a second surface, the second surface being opposite the first surface, the second surface having;
 d. an adhesive contacting the second surface of the absorbent body so as to form a region of positioning adhesive at the center of the second surface of the absorbent body, the region of positioning adhesive having a periphery;
 e. a backing layer adhered to the second surface of the absorbent body by the region of positioning adhesive, the backing layer having an inner zone at least partially surrounded by an outer zone,
 such that the periphery of the region of positioning adhesive defines an inner boundary of a surface area of the backing layer, such surface area of the backing layer extending from the periphery of the region of positioning adhesive in a direction away from periphery of the region of positioning adhesive, beyond at least a portion of the periphery of the absorbent body 1, to the outer zone of the backing layer, such surface area being free of or substantially free of adhesive.
30. The wound dressing assembly of embodiment 29 wherein the region of positioning adhesive is continuous.
31. The wound dressing assembly of embodiment 29 and/or 30 wherein the region of positioning adhesive is discontinuous.
32. The wound dressing assembly of any one of or combination of embodiments 29 to 31 wherein the absorbent body is in the form of a single layer or multilayer material.
33. The wound dressing assembly of any one of or combination of embodiments 29 to 32 wherein the absorbent body comprises creped cellulose wadding; melt blown polymers; chemically stiffened, modified or cross-linked cellulosic fibers; tissue; absorbent foams; absorbent sponges; superabsorbent polymers; absorbent gelling materials; or combinations of such materials.
34. The wound dressing assembly of any one of or combination of embodiments 29 to 33 wherein the absorbent body comprises a web produced by electrospinning; a nonwoven; a woven; a film; a batting; spunbond; spunlace; hydroentangled; carded; needle-punched; wetlaid or any other suitable material.
35. The wound dressing assembly of any one of or combination of embodiments 29 to 34 wherein the absorbent body comprises a foam material.
36. The wound dressing assembly of any one of or combination of embodiments 29 to 35 wherein the foam material comprises a polymer comprising one or more types of monomers or blend of polymers.
37. The wound dressing assembly of any one of or combination of embodiments 29 to 36 wherein the foam material is an open cell foam.
38. The wound dressing assembly of any one of or combination of embodiments 29 to 37 wherein the foam material is an open cell foam synthetic organic polymer selected from polyurethanes, carboxylated butadiene-styrene rubbers, polyesters, polyacrylates or mixtures thereof.
39. The wound dressing assembly of any one of or combination of embodiments 29 to 38 wherein the absorbent body comprises hydrocolloids.
40. The wound dressing assembly of any one of or combination of embodiments 29 to 39 wherein the hydrocolloids is selected from sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof and mixtures thereof
41. The wound dressing assembly of any one of or combination of embodiments 29 to 40 wherein the position adhesive contacts the second surface of absorbent body to form a continuous or discontinuous layer or surface area of positioning adhesive
42. The wound dressing assembly of any one of or combination of embodiments 29 to 41 wherein the backing layer has a periphery such that the periphery of the backing layer extends beyond at least a portion of the periphery of the absorbent body.
43. A wound dressing assembly comprising:
 b. an absorbent body having a longitudinally extending centerline, transversely extending centerline and a periphery, the absorbent body, having a first surface and a second surface, the second surface being opposite the first surface, the second surface having:

d. an adhesive contacting the second surface of the absorbent body so as to form a region of positioning adhesive extending substantially along the transversely extending centerline, e. a backing layer adhered to the second surface of the absorbent body by the region of positioning adhesive, the backing layer having an inner zone at least partially surrounded by an outer zone.

wherein the region of positioning adhesive has a first side and a second side, opposite the first side, such that when the region of positioning adhesive contacts the backing layer:

i. the first side defines an end of a first surface area of the backing layer extending from the first side, beyond the periphery of the absorbent body, to the outer zone of the backing layer in the direction of the longitudinally extending centerline; and ii. the second side defines an end of a second surface area of the backing layer extending from the second side, beyond the periphery of the absorbent body, to the outer zone of the backing layer in the direction of the longitudinally extending centerline and opposite the direction of the first surface area, the first and second surface areas being substantially free of adhesive.

44. The wound dressing assembly of embodiment 43 wherein the region of positioning adhesive is continuous.

45. The wound dressing assembly of embodiments 43 and/or 44 wherein the region of positioning adhesive is discontinuous.

46. The wound dressing assembly of any one of or combination of embodiments 43 to 45 wherein the absorbent body is in the form of a single layer or multilayer material.

47. The wound dressing assembly of any one of or combination of embodiments 43 to 46 wherein the absorbent body comprises creped cellulose wadding; melt blown polymers; chemically stiffened, modified or cross-linked cellulosic fibers; tissue; absorbent foams; absorbent sponges; superabsorbent polymers; absorbent gelling materials; or combinations of such materials.

48. The wound dressing assembly of any one of or combination of embodiments 43 to 47 wherein the absorbent body comprises a web produced by electrospinning; a nonwoven; a woven; a film; a batting; spunbond; spunlace; hydroentangled; carded; needle-punched; wetlaid or any other suitable material.

49. The wound dressing assembly of any one of or combination of embodiments 43 to 48 wherein the absorbent body comprises a foam material.

50. The wound dressing assembly of any one of or combination of embodiments 43 to 49 wherein the foam material comprises a polymer comprising one or more types of monomers or blend of polymers.

51. The wound dressing assembly of any one of or combination of embodiments 43 to 50 wherein the foam material is an open cell foam.

52. The wound dressing assembly of any one of or combination of embodiments 43 to 51 wherein the foam material is an open cell foam synthetic organic polymer selected from polyurethanes, carboxylated butadiene-styrene rubbers, polyesters, polyacrylates or mixtures thereof.

53. The wound dressing assembly of any one of or combination of embodiments 43 to 52 wherein the absorbent body comprises hydrocolloids.

54. The wound dressing assembly of any one of or combination of embodiments 43 to 53 wherein the hydrocolloids is selected from sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof and mixtures thereof 55. The wound dressing assembly of any one of or combination of embodiments 43 to 54 wherein the position adhesive contacts the second surface of absorbent body to form a continuous or discontinuous layer or surface area of positioning adhesive 56. The wound dressing assembly of any one of or combination of embodiments 43 to 55 wherein the backing layer has a periphery such that the periphery of the backing layer extends beyond at least a portion of the periphery of the absorbent body.

What is claimed is:

1. A wound dressing assembly comprising:

a. an absorbent body having a longitudinally extending centerline, transversely extending centerline and a periphery, the absorbent body, having a first surface and a second surface, the second surface being opposite the first surface:

b. an adhesive contacting the second surface of the absorbent body so as to form a region of positioning adhesive extending substantially along the transversely extending centerline the region of the positioning adhesive having a periphery, c. a backing layer adhered to the second surface of the absorbent body by the region of positioning adhesive, the backing layer having an inner zone at least partially surrounded by an outer zone wherein the region of positioning adhesive has a first side and a second side, opposite the first side, such that when the region of positioning adhesive contacts the backing layer:

i. the first side defines an end of a first surface area of the backing layer extending from the first side, beyond the periphery of the absorbent body, to the outer zone of the backing layer in the direction of the longitudinally extending centerline; and ii. the second side defines an end of a second surface area of the backing layer extending from the second side, beyond the periphery of the absorbent body, to the outer zone of the backing layer in the direction of the longitudinally extending centerline and opposite the direction of the first surface area, the first and second surface areas being substantially free of adhesive, and the periphery of the absorbent body being spaced away from the periphery of the region of positioning adhesive, whereby transfer of movement or stretch of the attached backing layer to absorbent body is minimized.

2. The wound dressing assembly of claim 1 wherein the region of positioning adhesive is continuous.

3. The wound dressing assembly of claim 1 wherein the region of positioning adhesive is discontinuous.

4. The wound dressing assembly of claim 1 wherein the absorbent body is in the form of a single layer or multilayer material.

5. The wound dressing assembly of claim 1 wherein the absorbent body comprises creped cellulose wadding; melt blown polymers; chemically stiffened, modified or cross-linked cellulosic fibers; tissue; absorbent foams; absorbent sponges; superabsorbent polymers; absorbent gelling materials; or combinations of such materials.

6. The wound dressing assembly of claim 1 wherein the absorbent body comprises a web produced by electrospinning; a nonwoven; a woven; a film; a batting; spunbond; spunlace; hydroentangled; carded; needle-punched; wetlaid or any other suitable material.

7. The wound dressing assembly of claim 5 wherein the absorbent body comprises a foam material.

8. The wound dressing assembly of claim 7 wherein the foam material comprises a polymer comprising one or more types of monomers or blend of polymers.

9. The wound dressing assembly of claim 7 wherein the foam material is an open cell foam.

10. The wound dressing assembly of claim 7 wherein the foam material is an open cell foam synthetic organic polymer selected from polyurethanes, carboxylated butadiene-styrene rubbers, polyesters, polyacrylates or mixtures thereof.

11. The wound dressing assembly of claim 1 wherein the absorbent body comprises hydrocolloids.

12. The wound dressing assembly of claim 11 wherein the hydrocolloids is selected from sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof and mixtures thereof.

13. The wound dressing assembly of claim 1 wherein the position adhesive contacts the second surface of absorbent body to form a continuous or discontinuous layer or surface area of positioning adhesive.

14. The wound dressing assembly of claim 1 wherein the backing layer has a periphery such that the periphery of the backing layer extends beyond at least a portion of the periphery of the absorbent body.

* * * * *